United States Patent
Kaye

(10) Patent No.: US 6,961,614 B2
(45) Date of Patent: Nov. 1, 2005

(54) DEVICE FOR DETECTING TACHYCARDIAC RHYTHM DISTURBANCES

(76) Inventor: Gerry C. Kaye, 55 West Ella Rd., Kirk Ella, Hull HU10 7QL (GB)

( * ) Notice: Subject to any disclaimer, the term of this patent is extended or adjusted under 35 U.S.C. 154(b) by 511 days.

(21) Appl. No.: 10/203,976

(22) PCT Filed: Feb. 19, 2001

(86) PCT No.: PCT/EP01/01827
§ 371 (c)(1),
(2), (4) Date: Oct. 24, 2002

(87) PCT Pub. No.: WO01/60451
PCT Pub. Date: Aug. 23, 2001

(65) Prior Publication Data
US 2003/0105494 A1 Jun. 5, 2003

(30) Foreign Application Priority Data
Feb. 17, 2000 (DE) .......................................... 100 08 324

(51) Int. Cl.[7] .................................................. A61N 1/18
(52) U.S. Cl. ......................................... 607/14; 600/547
(58) Field of Search .............................. 607/14, 17, 20, 607/24; 600/547

(56) References Cited

U.S. PATENT DOCUMENTS

| | | | |
|---|---|---|---|
| 4,303,075 A | 12/1981 | Heilman | |
| 5,179,946 A | 1/1993 | Weiss | |
| 5,184,615 A * | 2/1993 | Nappholz et al. | ............. 607/14 |
| 5,247,939 A | 9/1993 | Sjoquist | |
| 5,385,576 A | 1/1995 | Noren | |
| 5,427,112 A | 6/1995 | Noren | |
| 5,645,575 A | 7/1997 | Stangl | |
| 5,713,366 A * | 2/1998 | Armstrong et al. | ......... 600/510 |
| 5,755,742 A * | 5/1998 | Schuelke et al. | ............. 607/27 |
| 6,064,907 A | 5/2000 | Thong | |
| 6,154,674 A | 11/2000 | Meier | |
| 6,263,243 B1 | 7/2001 | Lang | |
| 6,317,633 B1 * | 11/2001 | Jorgenson et al. | ............ 607/28 |

FOREIGN PATENT DOCUMENTS

| | | |
|---|---|---|
| DE | 44 47 447 A1 | 7/1996 |
| DE | 196 09 362 C1 | 6/1997 |
| DE | 198 04 843 A1 | 8/1999 |
| EP | 0 009 255 A1 | 4/1980 |
| EP | 0 793 976 A2 | 3/1997 |
| WO | WO 98/14240 A1 | 4/1998 |

* cited by examiner

Primary Examiner—George Manuel
Assistant Examiner—Lenwood Faulcon, Jr.
(74) Attorney, Agent, or Firm—Hahn Loeser & Parks LLP

(57) ABSTRACT

A device for detecting tachycardiac rhythm disturbances, has a measuring unit for picking up and reproducing a measurement signal dependent on intracardial impedance at its output and an evaluation unit connected at the input to the measuring unit. The evaluation unit is adapted to output both a first signal which corresponds to the difference of a maximum and a minimum measurement signal within at least one predeterminable period of time and also a second signal which is dependent on the integral of the measurement signal over at least one predeterminable period of time.

69 Claims, 1 Drawing Sheet

DEVICE FOR DETECTING TACHYCARDIAC RHYTHM DISTURBANCES

The invention concerns a device for detecting tachycardiac rhythm disturbances, comprising a measuring unit for picking up and reproducing a measurement signal dependent on intracardial impedance at its output and an evaluation unit connected at the input to the measuring unit.

BACKGROUND OF THE ART

The invention further concerns an implantable electrostimulation device for the treatment of tachycardiac rhythm disturbances, comprising a detection unit, a control unit and a therapy unit which is adapted to produce a cardioversion or defibrillation electrotherapy to be transmitted to the heart, wherein the detection unit has a measuring unit for picking up and reproducing a measurement signal corresponding to intracardial impedance at its output and an evaluation unit connected at the input to the measuring unit and the control unit receives output signals from the evaluation unit and controls the activity of the measuring unit, the evaluation unit and the therapy unit.

By virtue of the lower specific resistance of blood in comparison with the myocardium tissue intracardial impedance varies with the volume of blood in the chambers of the heart, which changes in the course of the cardiac cycle. Thus, the pump activity of the heart can be monitored by evaluation of an intracardial impedance measurement and the existence of cardiac rhythm disturbances such as tachycardia or fibrillation can be inferred from variations in the amplitude pattern or the frequency of the periodic impedance signal.

Such a monitoring device is known from European patent application No. 0 009 255 A1, to Geddes, published 2 Apr. 1980. That publication discloses an implantable defibrillator having two measuring electrodes arranged at an axial spacing from each other at the distal end of a catheter which is introduced into the right ventricle. A control logic unit starts an intracardial impedance measurement procedure when automatic evaluation of an ECG signal indicates the possible existence of fibrillation. Impedance is determined by means of voltage measurement between the electrodes with an alternating current flow with a constant modulation amplitude and subsequent demodulation of the voltage signal. If the amplitude of the impedance signal indicates excessively low pump activity on the part of the heart defibrillation therapy is initiated.

A disadvantage with that device is that the signals from the measuring electrodes react sensitively to interference effects by virtue of their arrangement in a ventricle. Thus, body movement can already give rise to contact between the electrodes and the myocardium tissue. That means however that the measurement voltage and thus impedance measurement are falsified. Unnecessary defibrillation shocks which are painful to the patient can be the consequence of defective impedance measurement.

It is known from U.S. Pat. No. 5,427,112, to Noren, issued 27 Jun. 1995, for increasing the reliability of detection of cardiac rhythm disturbances, to record two signals and to monitor the in-phase periodic recurrence thereof, which is coupled to the heartbeat. In addition to measurement of the intracardial impedance signal, that known device also provides for determining the derivative thereof in respect of time. The impedance signal is recorded in a parameter representation as a function of its derivative in respect of time. The curve recorded in that way is compared to stored pattern curves, whereupon a decision is made about the necessity for and possibly the nature of a therapy. That procedure suffers from the disadvantage that it is highly costly in terms of computation and memory; it is firstly necessary to determine the derivative in respect of time of the measurement signal. The measurement value together with the derivative in respect of time have to be stored over at least the duration of a cardiac period. Then the phase position of the stored data has to be determined, in comparison with a previously stored pattern curve, and that requires extensive computations. Finally it is then necessary to form the difference of the measured pairs of values and corresponding pairs of values of the pattern curve, and ultimately evaluate same on the basis of a mathematical criterion.

U.S. Pat. No. 5,179,946, to Weiss, issued 19 Jan. 1993, discloses an implantable defibrillator in which, to increase the level of reliability of detection of cardiac rhythm disturbances, the intracardial impedance between two defibrillation electrodes fixed to the outside of the heart is measured. Adequate pump activity on the part of the heart is monitored on the basis of the impedance signal, by means of an amplitude discriminator. As an alternative to amplitude discrimination that known defibrillator provides for integration of the measured impedance signal. That device is complicated and expensive in circuitry terms because impedance measurement and tachycardia therapy are effected by way of the same electrodes. Therefore, avoiding destruction of the measuring unit by the high electrical voltages which are produced in a cardioversion or defibrillation procedure requires a protective circuit which is to be connected between the defibrillation electrodes and the measuring unit prior to application of the therapy. A disadvantage with that known defibrillator is also major operative involvement which stresses the patient when implanting the epicardial electrodes.

SUMMARY OF THE INVENTION

The object of the present invention is to provide a reliable but less complicated and expensive device for detecting tachycardiac rhythm disturbances and a less complicated and expensive implantable electrostimulation device for the treatment of tachycardiac rhythm disturbances.

In regard to an device for detecting tachycardiac rhythm disturbances that object is attained by the features of claim 1 and in regard to an implantable electrostimulation device for treating tachycardiac rhythm disturbances that object is attained by an device having the features of claim 20.

The basic idea of the invention is to increase the reliability of detection of cardiac rhythm disturbances by determining two signals which supplement each other in regard to their information content about cardiac activity and in that respect however at the same time use only such signals, for the determination of which the computing and memory demands are particularly low.

In the device according to the invention for detecting tachycardiac disturbances, based on the features of the classifying portion of claim 1, that is attained in that the evaluation unit is adapted to output both a first signal which corresponds to the difference of a maximum and a minimum measurement signal within at least one defined period of time and also a second signal which is dependent on the integral of the measurement signal over at least one defined period of time.

The defined period of time can extend over a predetermined period of time, for example 5 seconds, and/or over at least one cardiac cycle. The duration of a cardiac cycle can be determined for example in an electrocardiogram (ECG) as the period of time between two identical characteristic points of successive cardiac cycles, for example the Q-points.

The difference in the extreme values of the measurement signal within a cardiac cycle, that is to say the peak-to-peak amplitude PPA of the measurement signal indicates the difference between the intracardial impedance of the systolic and diastolic heart. During the systole there is a minimum amount of blood in the heart whereby the measured impedance assumes a maximum value within the cardiac period. During the diastole the heart contains a maximum amount of blood which causes the measured impedance to assume a minimum. The PPA is therefore a measurement in respect of the pump activity of the heart. When a tachycardia occurs the PPA of the intracardial impedance is significantly reduced by virtue of the reduced pump efficiency of the heart. In the case of a fibrillating heart the PPA of the intracardial impedance falls to approximately zero because the volume of blood in the heart is scarcely variable because of the uncoordinated movement of the heart muscles. In that respect the fall in the PPA below a predeterminable (patient-dependent) threshold value is a clear indication of the existence of a tachycardiac rhythm disturbance.

The PPA can be determined in a manner known to the man skilled in the art in a simple fashion and without complicated computations and without the storage of relatively large amounts of data.

Information about the pump activity of the heart is also collected by virtue of additionally determining, in accordance with the invention, a second signal which is dependent on the integral of the measurement signal over at least one defined period of time. When a tachycardia or defibrillation exists that second signal, by virtue of the worsened pump activity of the heart, assumes different values from the case involving a heart which is beating normally.

Integration of the measurement signal can also be implemented in per se known manner in a simple fashion and without involving memory complication and expenditure by virtue of the evaluation unit of the device according to the invention.

In addition it is advantageous that short-term deflections of the measurement signal have a substantially lesser effect on the second signal than on the PPA. Such deflections occur for example upon a variation in the position of measuring electrodes relative to the vessel walls of the heart. They can falsify the PPA by virtue of the fact that such a random, unusually high or low measurement signal forms the maximum or minimum during the measurement time interval, under some circumstances even a plurality of measurement time intervals in succession. Thus the first signal can incorrectly indicate the existence of a cardiac arrhythmia which does not exist. However, because of the relatively long period of time over which integration is effected such a deflection has an only slight influence on the integral of the measurement signal. In that case therefore the second signal will correctly indicate normal cardiac activity. That avoids unnecessary administration of a cardioversion or defibrillation therapy.

In that respect the items of information which the first and second signals furnish about cardiac activity supplement each other and provide for a high level of reliability in the detection of cardiac rhythm disturbances by the device according to the invention.

The first and the second signal can be determined by evaluation of the measurement signal within one or more periods of time. For example it is possible to briefly interrupt and then continue evaluation of the measurement signal. It is also possible to average the first or second signal which is determined over a plurality of periods of time.

The first and second signals however do not always have to be determined at the same time. For example it can also be provided that it is only when the first signal provides an indication of the existence of an arrhythmia that the additional determination of the second signal is implemented in a subsequent measurement step.

The duration of one or more cardiac cycles is desirable as the evaluation period of time. In that case, the operation of determining the start and stop times of the evaluation procedure relative to the cardiac cycle can be effected with per se known means. It is important that the device can alternatively evaluate over predetermined periods of time which are independent of the cardiac cycle as for example in a fibrillation situation triggering relative to the cardiac cycle cannot function.

The measures in accordance with the invention ensure on the one hand that electrostimulation therapy is also administered when there is an acute requirement. At the same time the invention avoids therapy which is unpleasant for the patient being unnecessarily administered solely by virtue of fluctuations in the measurement signal. The evaluation of two measurement signals which supplement each other in terms of their significance therefore affords a substantial increase in the level of reliability in the detection of tachycardiac rhythm disturbances. On the other hand both measurement signals can be easily determined; the evaluation thereof does not require any major computing expenditure. Simple comparison with reference values or reference value ranges already indicates the current condition of the heart.

In a preferred embodiment of the invention impedance measurement can be carried out in a unipolar mode. In unipolar impedance measurement, besides the measuring electrode which is introduced for example into the right ventricle, the implanted housing of the device is used at the same time as the second electrode. By virtue of the relatively large spacing between those electrodes, the unipolar impedance signal involves not just the information about the volume of blood in the heart. Rather for example information about the respiration rate is also included in the unipolar impedance signal. That can be used separately for ascertaining physiological parameters for example in the context of a pacemaker therapy. If it is only information about the pump activity of the heart that is to be processed, the low measurement signal frequencies occurring due to respiration (max. 1 Hz) can be easily separated from the higher-frequency component of the cardiac activity by suitable filtering of the signal.

Alternatively impedance measurement in the device according to the invention can also be implemented in a bipolar mode. In this case a measuring probe which is introduced into the heart will have two electrically mutually insulated electrodes. The flow of current induced in the measurement procedure is effected through the blood in the ventricle. The housing of the device does not play any part here.

In both cases the measuring unit has at least two electrodes of which at least one can be introduced into a chamber of the heart. In the case of unipolar measurement the second electrode is formed by an implantable housing of the device. In the case of bipolar measurement both electrodes are arranged directly in the region of the heart. In that case the second electrode can be arranged outside the heart, for example at the outside of the heart, or it can also be introduced into a chamber of the heart, but not necessarily into the same chamber as the first electrode. The essential point is that the flow of current in impedance measurement goes through a volume of blood within one or more chambers of the heart, that volume varying in the course of the cardiac period.

Preferably intracardial impedance can be determined in unipolar impedance measurement and also in bipolar impedance measurement by measurement of an electrical voltage between the electrodes when they are subjected to a preadjustable electrical current. Therefore the operation of determining impedance is effected on the basis of the preset current value and the measured voltage value in accordance with Ohm's law. The measuring unit accordingly has a current source. It is connected to the electrodes of the measuring unit in such a way that it produces a predetermined measuring current between them. The measuring current is, preferably of a pulsed nature, as will be described in greater detail hereinafter. In this embodiment the device also has voltage measuring means which are connected to the electrodes to measure an electrical voltage between the electrodes. In this embodiment impedance can be determined by division of the measurement signal by the current strength.

The amount of energy E(T) applied for impedance measurement during a predetermined period of time T, with a constant current I, can be calculated easily from the time integral, which is determined in any case, of the voltage U:

$$E(T) = I \times \int_T U(t) \, dt$$

The energy determined in that way can be evaluated as an additional information source.

Alternatively, in the device according to the invention, intracardial impedance can be determined by measurement of a flow of current between the electrodes when subjected to a preadjustable electrical voltage. For that purpose the measuring unit has a voltage source which is connected to the electrodes of the measuring unit in such a way that it produces a predetermined measuring voltage between them, and current measuring means which are connected to the electrodes to measure an electrical current between the electrodes.

In an embodiment of the invention, to avoid polarization of the electrode, the applied constant current strength or voltage can be modulated with a predeterminable time dependency in such a way that a period alternating current flows or a periodic ac voltage is applied, the maximum current strength of which or the maximum voltage amplitude of which is of the same value in each half-period. The pulse shape and frequency can be predetermined. Preferably an alternating current involving a square-wave pulse shape is used. In an embodiment, bipolar square-wave pulses with a time spacing of about 50 milliseconds are used. The positive and the immediately adjoining negative half-periods of the square-wave pulses each involve a duration of about 1 microsecond.

By virtue of the differing frequency dependency of the impedance of the blood and the myocardium tissue, the impedance contrast between systole and diastole can also be increased by a suitable choice of frequency in order to make evaluation of the PPA still more reliable, in terms of detecting cardiac arrhythmia. At a frequency of 4096 Hz approximately the specific resistance of blood is only a third of the specific resistance of the myocardium tissue.

In this embodiment the modulation of the measurement signal, which is caused by the frequency impressed on the measurement current or the measurement voltage respectively is preferably removed by a demodulation stage connected upstream of the time integration step. In operation of the device applied to the input of the demodulation stage is the measurement signal of the voltage measuring means (or current measuring means), which is modulated by the alternating current (or ac voltage) produced by the current source (or voltage source). The demodulation stage is designed in such a way that it is possible to take off at the output thereof a signal which corresponds in its configuration in respect of time to the envelope of the measurement signal or the positive or negative half-period of the measurement signal.

A further embodiment of the invention has control means which are adapted to cause the evaluation unit to start or stop integration of a signal at the input of the evaluation unit. The control means are preferably so designed that they cause the evaluation unit to effect integration over the respective period of time of one or some cardiac periods. For that purpose it is possible to have recourse to known trigger methods. In the case of a normally beating heart integration is started at a given phase point in the cardiac period so that normal, non-pathological frequency changes are not crucial in determining the integral of the measurement signal. The integration duration, that is to say the predetermined period of time T, is therefore adapted variably within certain limits to the cardiac frequency.

The control means however is preferably additionally so designed that it can cause the evaluation unit to effect integration over at least one respective predeterminable period of time which is independent of the duration of the cardiac period. That is required in the case of a fibrillating heart as triggering here is not possible. If triggering fails therefore, that is to be assessed as a first indication of arrhythmia. The device reacts to that situation by switching over to a predetermined fixed period of time for the integration operation. A new impedance measurement procedure is then started in order to check the condition of the heart.

In a further embodiment of the invention the evaluation unit has a memory. The evaluation unit is further so designed that, within the predetermined period of time, the hitherto maximum and minimum signals applied to the input of the evaluation unit are continuously determined and stored in the memory, that at the end of the period of time the difference between the currently stored maximum and minimum signals is calculated and that at the beginning of a respective subsequent period of time the signals last stored in the preceding period of time are erased from the memory. The memory therefore serves here only for temporarily receiving the values which are currently determined as the maximum and the minimum. They are overwritten as soon as a fresh maximum or minimum of the measurement signal is established within the measurement time interval. The operation of determining the extreme values can be re-started with each measurement period.

The period of time for which the operation of determining the PPA is executed is preferably also established by control means which are connected to the evaluation unit and which are so designed that they signal the evaluation unit the beginning and the end of the predetermined period of time.

In a particularly advantageous embodiment time control in respect of determining the first and second signals is effected centrally. The control means are correspondingly so designed that they cause the evaluation unit to effect integration and to determine the difference between the maximum and the minimum in each case within the same period of time. In that way, with the first and second signals, there are two partially complementary items of information about cardiac activity within the same period of time. Arrhythmia can be reliably and quickly diagnosed.

In a preferred embodiment the evaluation unit is so designed that, in operation of the device, at the end of the respective period of time, it outputs such a second signal which corresponds to the integral of the measurement signal over the period of time less the product of the duration of the period of time and the measurement signal minimum of the period of time.

In that way the significance of the second signal can be increased. That will be immediately apparent if it is considered that intracardial impedance of a fibrillating heart is approximately constant, because of the volume of blood which is little variable, and it assumes a value which is lower than the systolic impedance value but markedly higher than the diastolic impedance value of the heart. The time integral ZI of the intracardial impedance of the fibrillating heart will therefore differ only slightly from that of the normally beating heart over the same period of time T.

In order to increase significance therefore integration is effected over the difference between the current impedance value and a minimum impedance value $Z_0(T)$ which is individual for each integration period T. That value $Z_0(T)$ is in any case constantly fixed in the context of determining the PPA. That minimum impedance value $Z_0$ corresponds in the normal situation to the diastolic impedance signal. If therefore the intracardial impedance is denoted by Z, the integration interval by T and the second signal by ZI(T), then ZI(T) is given by:

$$ZI(T) = \int_T Z(t)\,dt - Z_0(T) \times T$$

For the sake of simplicity, without any loss in terms of mathematical accuracy, the differencing operation is effected downstream of integration and uses the minimum extreme value $Z_o(T)$ of intracardial impedance Z, which is fixed in the integration period T for determining the PPA.

In the case of a fibrillating heart the difference between $Z_o(T)$ and Z(t) is so slight that ZI(T) assumes a markedly lower value than in the case of a normally beating heart. In the condition of tachycardia it is admittedly possible to detect greater modulation of intracardial impedance than in the case of fibrillation, but the value of ZI(T) is still always markedly lower than in the case of a normally beating heart.

A further embodiment of the invention, for evaluation of the PPA and ZI signals, has a respective comparator which is connected to a first memory for reference values and/or reference value ranges and which is so designed that it compares the difference between successive extreme values or the time integral of the measurement signal to a respective reference value or reference value range contained in the first memory and produces an output signal which indicates whether the respective comparison result corresponds to a deviation from the reference value or reference value range or not, and possibly what deviation is involved. The two output signals of the comparators therefore indicate to a downstream-connected processing unit whether the respective signal is in the standard range or whether it deviates from the standard range. In the event of a deviation the amount by which and the direction in which the measurement signal deviates from the respective standard range can also be found from those output signals.

The reference values or reference value ranges which are stored in the first memory can be adaptive, that is to say variable, for example in accordance with the current physical activity, for further enhancing the reliability of detection of tachycardiac rhythm disturbances. For that purpose the memory content is influenced by a processing unit which analyzes the impedance signal by means of an algorithm, for example a "Regional Effective Slope Quality" (RQ-) algorithm (see Max Schaldach, Electrotherapy of the Heart, Springer Verdag, Berlin, Heidelberg, New York, 1992, pages 114 ff). For that purpose however the processing unit can also be adapted for processing further or other known signals which reflect physical activity.

The above-described advantages and features of the detection device according to the invention are of great benefit in an implantable electrostimulation device for the treatment of tachycardiac rhythm disturbances.

Particularly desirable is the integration of pacemaker functions into the therapy unit of the electrostimulation device, in addition to cardioversion/defibrillation. For that purpose the therapy unit of the electrostimulation device is so designed that it can optionally also apply a pacemaker electrostimulation therapy to the heart. The pacemaker therapy can be applied by way of the same electrode with which impedance is also measured. In that case no impedance measurement is effected during the duration of the stimulation pulse. The control unit implements the time control of the measuring unit and the therapy unit, which is required for that purpose.

A preferred embodiment of the electrostimulation device according to the invention additionally has a signal pattern memory which is connected to the control unit and in which one or more control signals for the measuring unit, the evaluation unit and/or the therapy unit are associated with signal patterns, that is to say output signals or combinations of output signals from the evaluation unit. The control unit is so designed that it compares output signals received from the evaluation unit to the signal patterns of the signal pattern memory and produces control signals associated with the respectively correct signal pattern and transmits them to the corresponding unit.

For example the control unit receives output signals from the evaluation unit, which indicate that the PPA value is 10% below the associated reference value range while the ZI value does not deviate from the reference value. The control unit compares that signal pattern to those stored in the signal pattern memory and recognizes from the entry which is correct in that case that a first control signal is to be sent to the measuring unit for again executing the operation of determining the PPA and ZI values, and a second control signal is to be sent to the therapy unit for continuing normal pacemaker therapy with the parameters applied hitherto. The control unit executes those steps.

Alternatively or supplemental to control of the electrostimulation device on the basis of the output signals of the evaluation unit by means of the signal pattern memory, the control unit can also access one or more assessment algorithms contained in a program memory in order to assess the output signals of the evaluation unit and to determine and produce the necessary control signals. A computing unit is provided for executing the assessment algorithm.

BRIEF DESCRIPTION OF THE FIGURE

Further advantages of the invention will be apparent from the description hereinafter of an embodiment with reference to the drawing.

DETAILED DESCRIPTION OF A PREFERRED EMBODIMENT

Figure 1:
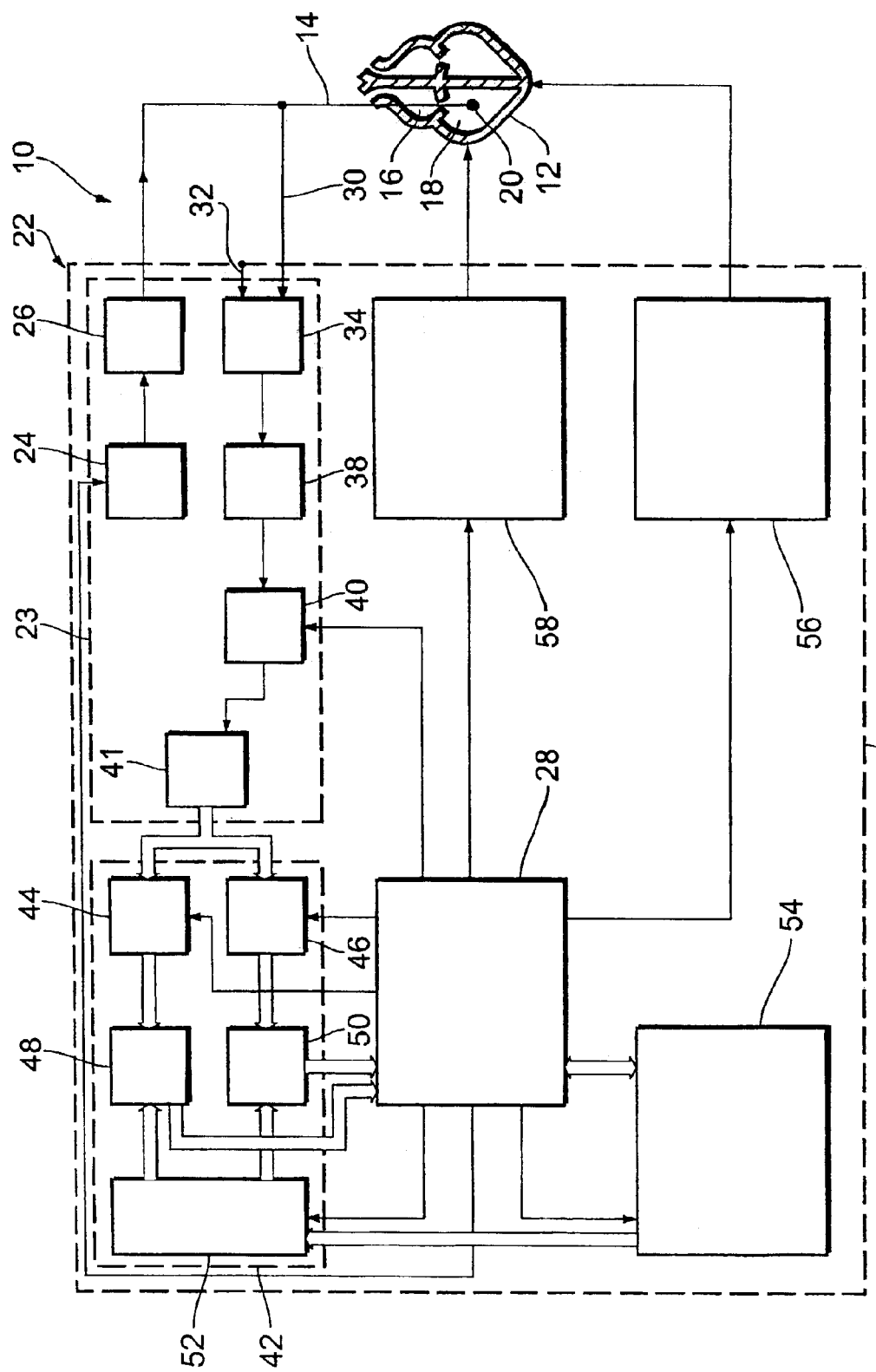
FIG. 1 shows a block diagram of an electrostimulation device according to the invention for treating tachycardiac rhythm disturbances with integrated pacemaker functions.

The stimulation device 10 shown in FIG. 1 involves an implantable integrated pacemaker and cardioverter/defibrillator which is used for the stimulation of a human heart 12.

For impedance measurement a measuring electrode 14 is introduced through the right atrium 16 into the right ventricle 18 of the heart 12. In the region of its distal end the measuring electrode 14 has an electrode 20 at which, in the impedance measurement procedure, an electrical measuring current issues into the right ventricle 18 or the blood contained therein.

The measuring current is an electrical alternating current of square-wave pulse shape and with the same value of current strength in both half-periods. The measuring current is produced within an assembly 22 in a measuring unit 23 by a current source 24 using a modulator 26. The function of the current source 24 is controlled by a central control 28 and synchronized with other functional procedures. For example the measuring electrode 20 can be used at the same time for stimulation of the right ventricle in the context of pacemaker therapy. Impedance measurement is then stopped by the control 28, for the duration of the stimulation pulse.

Impedance measurement is effected in a unipolar mode. Therefore the electrical voltage between the electrode 20 and the housing 36 of the assembly 22 is measured by way of suitable signal lines 30 and 32 by means of a voltmeter 34. The voltage signal is cleaned of the modulation frequency in a demodulator 38 connected on the downstream side thereof.

A filter stage 40 which can be selectively activated or deactivated by the control 28 serves to clean the measurement signal of frequency components in the range of up to about 1 Hz (respiration rate). The filtered measurement signal is then digitized by an A/D converter 41. The measuring unit 23 therefore outputs a digitized value corresponding to the measured voltage.

The voltage values outputted with the passage of time at the output of the measuring unit 23 are processed in an evaluation unit 22 in parallel in an extreme value analyzer 44 and in an integration and difference stage 46. The two evaluation stages 44 and 46 process the voltage values at the input of the evaluation unit 42 over equal periods of time. The length of that period of time is determined in each case by the control 28. It can determine the period of time on the basis of preceding events, computations or triggering.

The extreme value analyzer 44 compares the voltage value currently occurring at its input to a respective minimum and maximum value which have been previously put into intermediate storage. If the current voltage value is greater than the maximum value then that voltage value is written as a new maximum value into the intermediate memory and the old one is erased. If the current voltage value is less than the minimum value that minimum value is overwritten by the current voltage value. If neither of the two specified relationships is satisfied the procedure involves waiting for the next voltage value. In response to a signal from the control unit 28 the difference is formed between the maximum and the minimum values and outputted to a first comparator 48. The intermediate memories are generally erased for the beginning of evaluation of the measurement signal of a fresh measurement time period T, unless the control 28 caused only a short interruption in measurement.

In the integration and differentiation stage 46 the voltage values which successively occur at the input are integrated over an integration period which is monitored and established by the control 28. Integration is concluded in response to a corresponding signal from the control 28. The control 28 causes the extreme value analyzer 44 to output the set minimum value from the intermediate memory. Here too it is provided that integration is only to be suspended in response to a corresponding signal from the control 28 and continued in response to a further control signal without output being effected in the interim. In that way integration can be effected over a plurality of cardiac periods without recording deflections of the measurement signal which are caused by an electrical stimulation pulse.

The output signals from the extreme value analyzer 44 and the integration/difference stage 46 are compared in respective comparators 48 and 50 to reference values (or reference value ranges). For that purpose the comparators access a reference value memory 52 and form the difference between the output signal and the respective reference value (or the boundary values of the reference value range). The difference values formed in that way are transmitted to the control 28 by the evaluation unit 42 as results.

For assessment of the evaluation results the control 28 accesses a signal pattern memory 54. It contains signal patterns, that is to say output signals or combinations of output signals from the evaluation unit. Associated with each signal pattern in the signal pattern memory is one or more control signals serving for control of the measuring unit, the evaluation unit and/or the therapy unit, in a manner appropriate to the situation. The therapy unit Includes a pacemaker unit 56 and a cardioversion/defibrillation unit 58.

The output signals supplied by the evaluation unit are compared to the signal patterns of the signal pattern memory. The control ascertains from the signal pattern memory 54 which control signals are to be produced for which unit in relation to the respectively established signal pattern. In that way, depending on the respective situation established, measurement is repeated or a therapy is initiated or continued. A further reaction to the output signals of the evaluation unit 42 can also be adaptation of the reference value ranges, for example in the case of increased physical activity. For that purpose the new reference values (or reference value ranges) are taken from the signal pattern memory and written into the reference value memory 52.

Alternatively or in addition it is also possible to access an assessment algorithm which is stored in a program memory (not shown), for the execution of which by means of a computing unit (also not shown) the output signals of the evaluation unit are inputted as parameters. As above the control 28 obtains the control signals to be produced, as the result of execution of such an assessment algorithm.

What is claimed is:

1. A device for detecting tachycardiac rhythm disturbances, comprising:

a measuring unit for picking up and reproducing a measurement signal dependent on intracardial impedance at an output thereof; and an evaluation unit for detecting tachycardiac rhythm disturbances which is connected at an input side thereof to the measuring unit and which is adapted to determine an output a first signal which corresponds to the difference of a maximum and a minimum measurement signal within at least one defined period of time, wherein the evaluation unit is additionally adapted to determine and output a second signal which is dependent on the integral of the measurement signal over at least one defined second period of time, and the first signal associated with the second period of time, wherein the first-mentioned period of time is before the second period of time or is identical to the second period of time.

2. The device of claim 1, further comprising:
means for measuring unipolar impedance.

3. The device of claim 1, further comprising:
means for measuring bipolar impedance.

4. The device of claim 1, wherein the measuring unit comprises at least two electrodes, of which at least one can be introduced into a chamber of the heart.

5. The device of claim 4, further comprising:
a current source connected to the electrodes in such a way that it produces a predetermined measuring current between the electrodes; and
voltage measuring means connected to the electrodes for measuring an electrical voltage therebetween.

6. The device of claim 4, further comprising:
a voltage source connected to the electrodes in such a way that it produces a predetermined measuring voltage between the electrodes, and
current measuring means connected to the electrodes for measuring an electrical current therebetween.

7. The device of claim 5, wherein the current source is adapted to output an alternating current with a predetermined time dependency.

8. The device of claim 7, further comprising:
a demodulation device, at an input of which in operation of the device is the measurement signal of the voltage measuring means, which is modulated by the alternating current produced by the current source, the demodulation device being so designed that a signal can be taken off at an output, which corresponds in its configuration in respect of time to the envelope of the measurement signal or the positive or negative half-period of the measurement signal.

9. The device of claim 1, further comprising:
a filter stage for the removal of measurement signal components of a frequency of up to a maximum of 1 Hz.

10. The device of claim 1, further comprising:
control means adapted to cause the evaluation unit to start or stop integration of a signal at the input of the evaluation unit.

11. The device of claim 10, wherein the control means is so designed to cause the evaluation unit to effect integration respectively over the period of time of one or some cardiac periods.

12. The device of claim 10, wherein the control means is designed to cause the evaluation unit to effect integration over at least one respective predeterminable period of time which is independent of the cardiac period duration.

13. The device of claim 10, wherein the evaluation unit has a memory.

14. The device of claim 13, wherein the evaluation unit is so designed that within the predetermined period of time the hitherto maximum and minimum signals at the input of the evaluation unit are continuously determined and stored in the memory, that at the end of the period of time the difference between the currently stored maximum and minimum signals is calculated and that at the beginning of a respective subsequent period of time the signals last stored in the preceding period of time are erased from the memory.

15. The device of claim 14, wherein the control means is connected to the evaluation unit and designed to signal to the evaluation unit the beginning and the end of the predetermined period of time.

16. The device of claim 15, wherein the control means is designed to cause the evaluation unit to effect integration and to determine the difference between the maximum and the minimum respectively within the same period of time.

17. The device of claim 16, wherein the evaluation unit is so designed that in operation of the device at the end of the respective period of time the evaluation unit outputs a signal which corresponds to the integral of the measurement signal over the period of time less the product of the duration of the period of time and the measurement signal minimum of the period of time.

18. The device of claim 17, further comprising:
a respective comparator connected to a reference value memory containing reference values and/or reference value ranges and which is so designed that in operation of the device the comparator compares the difference of the extreme values or the time integral of the measurement signal to a respective reference value or reference value range contained in the reference value memory and produces an output signal which indicates whether the respective comparison result corresponds to a deviation from the reference value or reference value range or not and possibly what deviation is involved.

19. The device of claim 17, further comprising:
a respective comparator connected to a reference value memory containing fluctuation reference values and/or fluctuation reference value ranges and which is so designed that in operation of the device the comparator compares the change in the difference of the extreme values or the time integral of the measurement signal in relation to the respectively precedingly determined value to a respective fluctuation reference value or fluctuation reference value range contained in the reference value memory and produces an output signal which indicates whether the respective comparison result corresponds to a deviation from the fluctuation reference value or fluctuation reference value range or not and possibly what deviation is involved.

20. An implantable electrostimulation device for the treatment of tachycardiac rhythm disturbances comprising:
a detection unit;
a control unit;
a therapy unit for the treatment of tachycardiac rhythm disturbances adapted to produce a cardioversion or defibrillation electrotherapy to be applied to the heart,
wherein the detection unit comprises:
a measuring unit for picking up and reproducing a measurement signal corresponding to an intracardial impedance at an output thereof; and
an evaluation unit connected at an input to the measuring unit, and
wherein the control unit receives output signals from the evaluation unit and controls the activity of the measuring unit, the evaluation unit and the therapy unit, and
wherein the evaluation unit is adapted to determine and output a first signal which corresponds to the difference of a maximum and a minimum measured signal within at least one defined period of time, and
wherein the evaluation unit is additionally adapted to determine and output a second signal which is dependent on the integral of the measurement signal over at least one defined second period of time, and the first signal associated with the second period of time, wherein the first-mentioned period of time is before the second period of time or is identical to the second period of time.

21. The electrostimulation device of claim 20, wherein the therapy unit is so designed that it can also selectively apply a pacemaker electrostimulation therapy to the heart.

22. The electrostimulation device of claim 21, further comprising:
a signal pattern memory connected to the control unit and in which one or more control signals for the measuring unit, the evaluation unit and/or the therapy unit are associated with signal patterns, that is to say, output signals or combinations of output signals from the evaluation unit, and that the control unit is so designed that it compares output signals received from the evaluation unit to the signal patterns of the signal pattern memory and produces the control signals associated with the respectively correct signal pattern and transmits same to the corresponding unit.

23. The electrostimulation device of claim 22, wherein, for determining the control signals, the control unit additionally or exclusively accesses an assessment algorithm which is contained in a program memory and by means of which the control signals to be produced are computed in a computing unit on the basis of the output signals of the evaluation unit.

24. The electrostimulation device of claim 23, further comprising:
a housing which can be used as an electrode in the measurement of intracardial impedance.

25. The device of claim 2, wherein the measuring unit comprises at least two electrodes, of which at least one can be introduced into a chamber of the heart.

26. The device of claim 3, wherein the measuring unit comprises at least two electrodes, of which at least one can be introduced into a chamber of the heart.

27. The device of claim 25, further comprising:
a current source connected to the electrodes in such a way that it produces a predetermined measuring current between the electrodes; and
voltage measuring means connected to the electrodes for measuring an electrical voltage therebetween.

28. The device of claim 26, further comprising:
a current source connected to the electrodes in such a way that it produces a predetermined measuring current between the electrodes; and
voltage measuring means connected to the electrodes for measuring an electrical voltage therebetween.

29. The device of claim 25, further comprising:
a voltage source connected to the electrodes in such a way that it produces a predetermined measuring voltage between the electrodes, and
current measuring means connected to the electrodes for measuring an electrical current therebetween.

30. The device of claim 26, further comprising:
a voltage source connected to the electrodes in such a way that it produces a predetermined measuring voltage between the electrodes, and
current measuring means connected to the electrodes for measuring an electrical current therebetween.

31. The device of claim 6, wherein the voltage source is adapted to output an ac voltage with a predetermined time dependency.

32. The device of claim 27, wherein the current source is adapted to output an alternating current with a predetermined time dependency.

33. The device of claim 28, wherein the current source is adapted to output an alternating current with a predetermined time dependency.

34. The device of claim 29, wherein the voltage source is adapted to output an ac voltage with a predetermined time dependency.

35. The device of claim 30, wherein the voltage source is adapted to output an ac voltage with a predetermined time dependency.

36. The device of claim 31, further comprising:
a demodulation device, at an input of which in operation of the device is the measurement signal of the current measuring means, which is modulated by the ac voltage produced by the voltage source, the demodulation device being so designed that a signal can be taken off at an output, which corresponds in its configuration in respect of time to the envelope of the measurement signal or the positive or negative half-period of the measurement signal.

37. The device of claim 32, further comprising:
a demodulation device, at an input of which in operation of the device is the measurement signal of the voltage measuring means, which is modulated by the alternating current produced by the current source, the demodulation device being so designed that a signal can be taken off at an output, which corresponds in its configuration in respect of time to the envelope of the measurement signal or the positive or negative half-period of the measurement signal.

38. The device of claim 33, further comprising:
a demodulation device, at an input of which in operation of the device is the measurement signal of the voltage measuring means, which is modulated by the alternating current produced by the current source, the demodulation device being so designed that a signal can be taken off at an output, which corresponds in its configuration in respect of time to the envelope of the measurement signal or the positive or negative half-period of the measurement signal.

39. The device of claim 34, further comprising:
a demodulation device, at an input of which in operation of the device is the measurement signal of the current measuring means, which is modulated by the ac voltage produced by the voltage source, the demodulation device being so designed that a signal can be taken off at an output, which corresponds in its configuration in respect of time to the envelope of the measurement signal or the positive or negative half-period of the measurement signal.

40. The device of claim 35, further comprising:
a demodulation device, at an input of which in operation of the device is the measurement signal of the current measuring means, which is modulated by the ac voltage produced by the voltage source, the demodulation device being so designed that a signal can be taken off at an output, which corresponds in its configuration in respect of time to the envelope of the measurement signal or the positive or negative half-period of the measurement signal.

41. The device of claim 37, further comprising:
a filter stage for the removal of measurement signal components of a frequency of up to a maximum of 1 Hz.

42. The device of claim 39, further comprising:
a filter stage for the removal of measurement signal components of a frequency of up to a maximum of 1 Hz.

43. The device of claim 41, further comprising:
control means adapted to cause the evaluation unit to start or stop integration of a signal at the input of the evaluation unit.

44. The device of claim 42, further comprising:
control means adapted to cause the evaluation unit to start or stop integration of a signal at the input of the evaluation unit.

45. The device of claim 43, wherein the control means is so designed to cause the evaluation unit to effect integration respectively over the period of time of one or some cardiac periods.

46. The device of claim 44, wherein the control means is so designed to cause the evaluation unit to effect integration respectively over the period of time of one or some cardiac periods.

47. The device of claim 11, wherein the control means is designed to cause the evaluation unit to effect integration over at least one respective predeterminable period of time which is independent of the cardiac period duration.

48. The device of claim 43, wherein the control means is designed to cause the evaluation unit to effect integration over at least one respective predeterminable period of time which is independent of the cardiac period duration.

49. The device of claim 44, wherein the control means is designed to cause the evaluation unit to effect integration over at least one respective predeterminable period of time which is independent of the cardiac period duration.

50. The device of claim 45, wherein the control means is designed to cause the evaluation unit to effect integration over at least one respective predeterminable period of time which is independent of the cardiac period duration.

51. The device of claim 46, wherein the control means is designed to cause the evaluation unit to effect integration over at least one respective predeterminable period of time which is independent of the cardiac period duration.

52. The device of claim 50, wherein the evaluation unit has a memory.

53. The device of claim 51, wherein the evaluation unit has a memory.

54. The device of claim 52, wherein the evaluation unit is so designed that within the predetermined period of time the hitherto maximum and minimum signals at the input of the evaluation unit are continuously determined and stored in the memory, that at the end of the period of time the difference between the currently stored maximum and minimum signals is calculated and that at the beginning of a respective subsequent period of time the signals last stored in the preceding period of time are erased from the memory.

55. The device of claim 53, wherein the evaluation unit is so designed that within the predetermined period of time the hitherto maximum and minimum signals at the input of the evaluation unit are continuously determined and stored in the memory, that at the end of the period of time the difference between the currently stored maximum and minimum signals is calculated and that at the beginning of a respective subsequent period of time the signals last stored in the preceding period of time are erased from the memory.

56. The device of claim 54, wherein the control means is connected to the evaluation unit and designed to signal to the evaluation unit the beginning and the end of the predetermined period of time.

57. The device of claim 55, wherein the control means is connected to the evaluation unit and designed to signal to the evaluation unit the beginning and the end of the predetermined period of time.

58. The device of claim 56, wherein the control means is designed to cause the evaluation unit to effect integration and to determine the difference between the maximum and the minimum respectively within the same period of time.

59. The device of claim 57, wherein the control means is designed to cause the evaluation unit to effect integration and to determine the difference between the maximum and the minimum respectively within the same period of time.

60. The device of claim 58, wherein the evaluation unit is so designed that in operation of the device at the end of the respective period of time the evaluation unit outputs a signal which corresponds to the integral of the measurement signal over the period of time less the product of the duration of the period of time and the measurement signal minimum of the period of time.

61. The device of claim 59, wherein the evaluation unit is so designed that in operation of the device at the end of the respective period of time the evaluation unit outputs a signal which corresponds to the integral of the measurement signal over the period of time less the product of the duration of the period of time and the measurement signal minimum of the period of time.

62. The device of claim 60, further comprising:
a respective comparator connected to a reference value memory containing reference values and/or reference value ranges and which is so designed that in operation of the device the comparator compares the difference of the extreme values or the time integral of the measurement signal to a respective reference value or reference value range contained in the reference value memory and produces an output signal which indicates whether the respective comparison result corresponds to a deviation from the reference value or reference value range or not and possibly what deviation is involved.

63. The device of claim 61, further comprising:
a respective comparator connected to a reference value memory containing reference values and/or reference value ranges and which is so designed that in operation of the device the comparator compares the difference of the extreme values or the time integral of the measurement signal to a respective reference value or reference value range contained in the reference value memory and produces an output signal which indicates whether the respective comparison result corresponds to a deviation from the reference value or reference value range or not and possibly what deviation is involved.

64. The device of claim 60, further comprising:
a respective comparator connected to a reference value memory containing fluctuation reference values and/or fluctuation reference value ranges and which is so designed that in operation of the device the comparator compares the change in the difference of the extreme values or the time integral of the measurement signal in relation to the respectively precedingly determined value to a respective fluctuation reference value or fluctuation reference value range contained in the reference value memory and produces an output signal which indicates whether the respective comparison result corresponds to a deviation from the fluctuation reference value or fluctuation reference value range or not and possibly what deviation is involved.

65. The device of claim 61, further comprising:
a respective comparator connected to a reference value memory containing fluctuation reference values and/or fluctuation reference value ranges and which is so designed that in operation of the device the comparator compares the change in the difference of the extreme values or the time integral of the measurement signal in relation to the respectively precedingly determined value to a respective fluctuation reference value or fluctuation reference value range contained in the reference value memory and produces an output signal which indicates whether the respective comparison result corresponds to a deviation from the fluctuation reference value or fluctuation reference value range or not and possibly what deviation is involved.

66. The electrostimulation device of claim 20, further comprising:

a signal pattern memory connected to the control unit and in which one or more control signals for the measuring unit, the evaluation unit and/or the therapy unit are associated with signal patterns, that is to say, output signals or combinations of output signals from the evaluation unit, and that the control unit is so designed that it compares output signals received from the evaluation unit to the signal patterns of the signal pattern memory and produces the control signals associated with the respectively correct signal pattern and transmits same to the corresponding unit.

67. The electrostimulation device of claim 22, wherein, for determining the control signals, the control unit additionally or exclusively accesses an assessment algorithm which is contained in a program memory and by means of which the control signals to be produced are computed in a computing unit on the basis of the output signals of the evaluation unit.

68. The electrostimulation device of claim 23, further comprising:

a housing which can be used as an electrode in the measurement of intracardial impedance.

69. The electrostimulation device of claim 20, further comprising:

a housing which can be used as an electrode in the measurement of intracardial impedance.

* * * * *